(12) United States Patent
Rahlf et al.

(10) Patent No.: US 9,555,204 B2
(45) Date of Patent: Jan. 31, 2017

(54) METHOD FOR CONTROLLING THE END-EXPIRATORY PRESSURE IN A RESPIRATORY SYSTEM

(75) Inventors: Till Rahlf, Stockelsdorf (DE); Ralf Heesch, Lübeck (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 689 days.

(21) Appl. No.: 13/992,850

(22) PCT Filed: Feb. 3, 2012

(86) PCT No.: PCT/EP2012/000495
§ 371 (c)(1),
(2), (4) Date: Jun. 10, 2013

(87) PCT Pub. No.: WO2013/004317
PCT Pub. Date: Jan. 10, 2013

(65) Prior Publication Data
US 2013/0255687 A1 Oct. 3, 2013

(30) Foreign Application Priority Data
Jul. 2, 2011 (DE) ........................ 10 2011 106 406

(51) Int. Cl.
| A61M 16/00 | (2006.01) |
| A61M 16/20 | (2006.01) |
| A61M 16/01 | (2006.01) |
| A61M 16/08 | (2006.01) |
| A61M 16/10 | (2006.01) |
| A61M 16/18 | (2006.01) |
| A61M 16/22 | (2006.01) |

(52) U.S. Cl.
CPC ......... *A61M 16/00* (2013.01); *A61M 16/0069* (2014.02); *A61M 16/01* (2013.01);
(Continued)

(58) Field of Classification Search
CPC ............ A61M 16/205; A61M 16/0891; A61M 16/2833; A61M 2016/103; A61M 16/0069; A61M 16/01; A61M 16/104; A61M 2016/0042; A61M 2016/0039
See application file for complete search history.

(56) References Cited

U.S. PATENT DOCUMENTS 4,082,093 A    4/1978  Fry et al.
5,575,283 A *  11/1996 Sjoestrand ............ A61M 16/00
                                                    128/204.18
(Continued)

FOREIGN PATENT DOCUMENTS

CN    101884822 A   11/2010
DE     293 268 A5    8/1991
(Continued)

*Primary Examiner* — Justine Yu
*Assistant Examiner* — Douglas Sul
(74) *Attorney, Agent, or Firm* — McGlew and Tuttle, P.C.

(57) ABSTRACT

A method for controlling the end-expiratory pressure at a patient (30) in a respiratory system (50) of an anesthesia apparatus or respirator (30) includes regulating a pressure curve (401a, 401b, 501a, 501b) during the expiration phase (650) of the patient such that the pressure curve is described by an at least partially dropping curve (105a, 105b, 106a, 106b, 601, 602, 603, 604) from a first upper pressure value (613a, 613b, 613c, 613d) to a first lower pressure value (614a, 614b, 614c, 614d) from the end of the inspiration phase (660) until the beginning of the next, following inspiration phase (670). An anesthesia apparatus or respirator is provided that includes an operating and actuating unit that regulates a controllable expiratory valve and a respiration drive such that the pressure curve is described by an at least partially dropping curve.

17 Claims, 9 Drawing Sheets

(52) U.S. Cl.
CPC ...... *A61M 16/085* (2014.02); *A61M 16/0833* (2014.02); *A61M 16/0891* (2014.02); *A61M 16/205* (2014.02); *A61M 16/009* (2013.01); *A61M 16/0078* (2013.01); *A61M 16/104* (2013.01); *A61M 16/18* (2013.01); *A61M 16/22* (2013.01); *A61M 2016/0021* (2013.01); *A61M 2016/0027* (2013.01); *A61M 2016/0039* (2013.01); *A61M 2016/0042* (2013.01); *A61M 2016/103* (2013.01); *A61M 2230/432* (2013.01)

(56) References Cited

U.S. PATENT DOCUMENTS

| | | | | |
|---|---|---|---|---|
| 6,345,619 B1 * | 2/2002 | Finn | ...................... | A61M 16/00 128/204.18 |
| 6,564,798 B1 * | 5/2003 | Jalde | ...................... | A61M 16/20 128/200.24 |
| 6,640,806 B2 * | 11/2003 | Yurko | ................... | A61M 16/00 128/200.26 |
| 8,397,720 B2 * | 3/2013 | Eger | ................. | A61M 16/0051 128/200.24 |
| 2006/0037616 A1 | 2/2006 | Seeger et al. | | |
| 2008/0091117 A1 | 4/2008 | Choncholas et al. | | |
| 2008/0105260 A1 | 5/2008 | Heesch | | |
| 2010/0275920 A1 * | 11/2010 | Tham | ................ | A61M 16/0051 128/204.23 |

FOREIGN PATENT DOCUMENTS

| | | |
|---|---|---|
| DE | 10 2004 039 711 B3 | 5/2006 |
| GB | 2 417 206 A | 2/2006 |
| WO | 2010/108552 A1 | 9/2010 |
| WO | 2010/130290 A1 | 11/2010 |

* cited by examiner

US 9,555,204 B2

METHOD FOR CONTROLLING THE END-EXPIRATORY PRESSURE IN A RESPIRATORY SYSTEM

CROSS REFERENCE TO RELATED APPLICATIONS

This application is a U.S. National Phase Application of International Application PCT/EP2012/000495 filed Feb. 3, 2012 and claims the benefit of priority under 35 U.S.C. §119 of German Patent Application DE 10 2011 106 406.4 filed Jul. 2, 2011, the entire contents of which are incorporated herein by reference.

FIELD OF THE INVENTION

The present invention pertains to a method for controlling an end-expiratory pressure at the end of the expiration phase, the so-called expiration phase of a patient in a respiratory system of an anesthesia apparatus or of a respirator (ventilator).

BACKGROUND OF THE INVENTION

During the mechanical respiration of a patient by means of an anesthesia apparatus or a respirator, the pressure is reduced at the end of expiration to the extent that the patient can breathe out. The pressure level is not lowered now completely to the prevailing ambient pressure, but there remains a residual pressure, the so-called positive end-expiratory pressure (PEEP), in the lung. This pressure is maintained at a constant level by means of the anesthesia apparatus or respirator during expiration until the next inspiration. Any possible leaks in the connection from the anesthesia apparatus or respirator to the patient are compensated by a pressure regulator by the pressure regulator adjusting a volume by means of supplying a rate of flow to the extent that the positive end-expiratory pressure can be maintained in the patient's lungs. Due to this slight overpressure in the lungs against the ambient pressure, it is ensured by a distension of the lungs that the opened areas in the lungs will not collapse again during expiration during the time until the next inspiration and the exchange area of the lungs will not be reduced hereby.

A suctioning measuring system is connected in many cases by means of a flexible tube in anesthesia systems directly at the connection piece to the patient, in which the expiratory and inspiratory breathing tubes are brought together, the so-called Y-piece, and gas is sent with a suction volume flow directly from the patient into the measuring system, and the physiological respiration parameters of the patient are analyzed in the measuring system. For example, the oxygen concentration and the carbon dioxide concentration ($C_{CO_2}$) are recorded over time. Especially the carbon dioxide concentration ($C_{CO_2}$) at the end of expiration by the patient, the so-called end-tidal concentration ($etCO_2$), is of diagnostic and therapeutic significance here. This makes it possible to infer how sufficient the patient's respiration, i.e., the supply with oxygen, is. The physician makes decisions about adjusting the respiration, for example, the respiration rate, the minute volume, the pressure settings, as well as the selected, administered oxygen concentration.

The adjustment of the positive end-expiratory pressure by a pressure regulator in the respiratory system causes fresh gas to be delivered directly to the patient to the so-called Y-piece. This fresh gas mixes there with the air expired by the patient. This mixed air is suctioned off from the patient, from the Y-piece, to the measuring arrangement. The suctioning takes place typically with a suction line, typically by means of a very thin suction tube with an internal diameter in the range of 0.5 mm to 1.5 mm over a length of 1.5-3.0 m. A suction volume flow of typically about 0.2 L/minute delivers the air through the suction tube from the patient into the measuring arrangement. The gas thus reaches the measuring arrangement with a delay in the range of about 0.8 sec to 3.5 sec due to its path and the type of suctioning. If additional components with an additional volume, for example, a water trap, are arranged in the suction line on the path to the measuring arrangement, and if the volume in the measuring arrangement itself, as well as the necessary measuring time for determining the carbon dioxide concentration in the measuring arrangement are taken into account, the delay between the location of the test sample at the patient and a value of a carbon dioxide concentration, which value is determined by measurement and displayed, increases, on the whole, to a value in the range of about 3 sec to 10 sec.

Such a delay corresponds approximately to a number ranging from less than one breathing cycle to two breathing cycles for an adult, to 1 to 6 breathing cycles for an infant as well as to 3 to 10 breathing cycles for a newborn.

Depending on the type of pressure regulation and the situation prevailing at the patient, at the respiratory system, the respiration parameters selected and the leaks present in the system, the regulated adjustment of the positive end-expiratory pressure causes the carbon dioxide concentration ($C_{CO_2}$) at the measuring arrangement not to correspond to the concentration that is present in the pharyngeal space and the bronchial space of the patient during expiration. A respiratory system with a regulator for setting a positive end-expiratory pressure is known from the document U.S. Pat. No. 4,082,093.

SUMMARY OF THE INVENTION

An object of the present invention is to provide a method that makes it possible to set the positive end-expiratory pressure in a respiratory system of a respirator or anesthesia apparatus such that the measured values of the carbon dioxide concentration ($C_{CO_2}$) in the $CO_2$ measuring arrangement are not affected by the pressure regulation.

According to the invention, a method is provided for controlling the end-expiratory pressure at a patient in a respiratory system of an anesthesia apparatus or respirator. A pressure curve is regulated during the expiration phase of the patient such that the pressure curve is described by an at least partially dropping curve from a first upper pressure value to a first lower pressure value from the end of the inspiration phase until the beginning of the next, following inspiration phase.

According to another aspect of the invention, an anesthesia apparatus or respirator is provided comprising a patient connection, a gas pressure regulating arrangement for regulating gas pressure at the patient connection and an operating and actuating unit. The operating and actuating unit is connected to the gas pressure regulating arrangement for regulating pressure to the patient during an inspiration phase and during an expiration phase such. The expiration phase, from the end of the inspiration phase to the beginning of the following inspiration phase, is described by an at least partially dropping curve from an upper pressure value to a lower pressure value.

Provisions are made in the manner according to the present invention for the control circuit for the positive end-expiratory pressure in the respiratory system of an anesthesia apparatus or respiratory system to be controlled in such a manner that the mixing at the Y-piece does not affect the measured values of the suctioning gas concentration measurement, especially of the $CO_2$ measurement. The pressure regulator is controlled such that the positive end-expiratory pressure for the breathing-out phase—the so-called expiration phase—of the patient is not maintained at an absolutely constant pressure level, but the pressure level of the positive end-expiratory pressure (PEEP) at the end of the expiration phase is selected to be lower than the pressure level of the positive end-expiratory pressure (PEEP) at the beginning of the expiration phase and is stabilized. Instead of a constant pressure level, a dropping pressure ramp is used to this end according to the present invention for the regulation as a set value for the pressure regulator of the positive end-expiratory pressure (PEEP) in the course of the expiration phase. The pressure levels at the end and at the beginning of the expiration phase are preferably determined in this case from a predetermined mean value of the positive end-expiratory pressure (PEEP). The pressure regulation is not affected according to the present invention during the breathing-in phase, the so-called inspiration phase.

In a first embodiment of the present invention, the dropping pressure ramp is described by a first upper pressure value and a first lower pressure value. The mean value between the first upper pressure value and the first lower pressure value represents the desired positive end-expiratory pressure, so that there is no change for the patient in the pressure ratio present relative to the ambient pressure as an average compared to a constant positive end-expiratory pressure stabilized at a constant pressure level over the duration of the expiration phase.

The duration of the expiration phase and of the inspiration phase is defined by the respiration parameters selected, such as the respiration rate combined with the so-called I/E ratio, i.e., the ratio of the inspiration phase to the expiration phase. The first upper pressure value and the first lower pressure value are determined from this duration of the expiration phase and the desired positive end-expiratory pressure value set by the user. In a preferred embodiment, the determination of the first upper pressure value and of the first lower pressure value is described by a linearly dropping pressure curve or by a nonlinearly dropping pressure curve during the expiration phase.

A linear curve also includes, in the sense of the present invention, any curve that obeys a linear equation of a straight line. A nonlinear curve also includes, in the sense of the present invention, any curve that obeys a square or cubic function or a higher-order polynomial. Also included are, furthermore, logarithmic or exponential curves as well as generally progressively or degressively dropping functions, which are suitable for determining a first upper pressure value and a first lower pressure value from the duration of the expiration phase and the mean, desired value for the positive end-expiratory pressure.

The function is discontinuous in another preferred embodiment. This means that a linearly dropping function or a nonlinearly dropping function does not have a continuous curve with dropping slope, but the curve is stepped. The positive end-expiratory pressure is lowered in this variant from a first upper pressure level in steps to a first lower pressure level, and the mean level of the positive end-expiratory pressure, which was selected by the user for the patient in question, will again become established as the mean value between the first upper pressure level and the first lower pressure level.

In another preferred embodiment of the present invention, the dropping curve from a first upper pressure level to a first lower pressure level does not take place over the entire duration of the expiration phase. The curve of the positive end-expiratory pressure is partially constant and partially dropping in this further preferred embodiment. The positive end-expiratory pressure is maintained at an upper pressure level at the beginning of the expiration phase for a certain duration at the end of the inspiration phase in this further preferred embodiment. Beginning from a certain time during the expiration phase, the pressure is lowered from the upper pressure level to a lower pressure level according to a dropping curve. This leads to a combination of an upper, constant pressure level for a time delay of a predetermined duration at the beginning of the expiration phase with a subsequent drop in pressure, so that a stronger gradient is obtained from the upper pressure level to the lower pressure level for the remaining duration of the expiration phase. In this further preferred embodiment according to the present invention, this increased pressure gradient causes the phase during which the $CO_2$-containing air is delivered from the patient's lungs into his oral cavity to the Y-piece to be prolonged for the patient. This variant is especially advantageous if the expiration times are comparatively long, i.e., such a control according to a dropping pressure curve with a constant component preceding the time delay is especially advantageous in case of low respiration rates of 6-10 breaths per minute.

The settings on the anesthesia apparatus and respirator, which the user has made for controlling the respiration of the patient, namely, the preset PEEP settings themselves, preferably in the form of a preset mean PEEP value ($\overline{PEEP}$), as well as the ratio of the inspiration time to the expiration time, the so-called I/E ratio, and the respiration rate RR, are also taken into account for designing the pressure curve during the expiration phase in another preferred embodiment.

In another preferred embodiment, the properties of the measuring device are taken into account as well. Both the length of the tube, the diameter of the tube and the suction volume flow are taken into account as well. The volume of gas that reaches the measuring means as a quantity of gas from the patient, namely, from the Y-piece, in the tube to the measuring device, is obtained from the length of the tube and the diameter of the tube. The time delay that occurs from the Y-piece and the pressure and concentration values present there until this quantity of air arrives at the measuring arrangement for the analysis is obtained from the suction volume flow and the volume. This suction time delay is taken into account in this preferred embodiment by coordinating the selection of the time delay at the beginning of the expiration time and also the selection of the upper pressure value and of the lower pressure value with the measuring time delay for the $CO_2$ measurement.

The measuring time needed in the measuring arrangement for the determination and selection of the time delay at the beginning of the expiration time and of the upper as well as lower pressure values is also taken into account in another preferred embodiment.

Typical values for an upper pressure value and a lower pressure value for a linearly dropping pressure curve during the expiration phase, which are typical parameter settings for the respiration rate, positive end-expiratory pressure and I/E ratio for three different types of patients, are shown below. A typical value for the three selected patient types is set as the mean positive end-expiratory pressure. The three patient types differ essentially in that the respiration must be performed according to different criteria and with different parameter settings, because the lungs of the patients are different in terms of their pneumatic properties. These include the volume, compliance and pneumatic resistance. The pneumatic properties of patients can be assigned to different patient types in a simplified manner based on the body weight.

These three patient types include as a first example an adult with a typical body weight of about 70 kg, and a child with a typical body weight of about 10 kg is selected as a second example, and a newborn baby with a typical body weight about 2 kg is selected as a third example.

Different values are obtained for the lung volume and different respiration rates are obtained for these three patient types, and they result in different conditions for the respiration.

Table 1 below shows typical mean values for body weight, lung volume V, minute volume MV, respiration rate RR, I/E ratio, inspiration time $T_i$, expiration time $T_e$ and inspiration pressure $P_{insp}$ as well as expiration pressure (PEEP).

TABLE 1

| Body weight | V [mL] | MV [L] | RR [1/minute] | I/E ratio | $P_{insp}$ [hPa] | PEEP [hPa] | $T_i$ [sec] | $T_e$ [sec] |
|---|---|---|---|---|---|---|---|---|
| ~70 kg | 600 | 4.8 | 8 | 1:2 | 15 | 5 | 2.5 | 5 |
| ~10 kg | 200 | 3.0 | 15 | 1:2 | 15 | 5 | 1.33 | 2.66 |
| ~2 kg | 30 | 1.5 | 50 | 1:1 | 15 | 5 | 0.6 | 0.6 |

Assuming a linear curve in this calculation example, a first upper pressure value and a first lower pressure value can then be determined from the values in this table.

Table 2 below shows typical mean values for an upper pressure value ($PEEP_{High}$) and a lower pressure value ($PEEP_{Low}$) for the three patient types, namely, adult, child and newborn baby.

TABLE 2

| Body weight | PEEP [hPa] | $PEEP_{High}$ [hPa] | $PEEP_{Low}$ [hPa] |
|---|---|---|---|
| ~70 kg | 5 | 5.2 | 4.8 |
| ~10 kg | 5 | 5.2 | 4.8 |
| ~2 kg | 5 | 3.2 | 2.8 |

An exemplary calculation was performed here for the special embodiment with a time delay at the beginning of the expiration phase, before the dropping pressure ramp starts, for the first example with an adult of 70 kg according to Tables 1 and 2.

With the data as boundary conditions according to Tables 1 and 2 and with the selected time delay corresponding to half the expiration time of 5 sec, i.e., a time delay of 2.5 sec, a first upper pressure value of 5.2 hPa and a first lower pressure value of 4.8 hPa are obtained for an adult with a body weight of 70 kg for the regulation of the positive end-expiratory pressure during the expiration phase of a patient.

Due to the use of the time delay at the beginning of the expiration phase, the pressure gradient becomes steeper towards the end of the expiration phase compared to the embodiment with a pressure ramp that already drops at the beginning of the expiration phase. The steeper pressure gradient causes the patient to be able to expire nearly until the end of the expiration, so that the measurement of the carbon dioxide concentration can also take place towards the end of the expiration without mixing with the inspiration gas.

The setting of the upper pressure value and of the lower pressure value can be performed for the special embodiment with a time delay at the beginning of the expiration phase before the start of the dropping pressure ramp in the same manner as in case of the use of the dropping pressure ramp without a time delay, so that the time delay leads, as was described above, merely to a steeper pressure gradient.

However, it is also possible in one technical embodiment, and this possibility is also covered by the present invention, to lower the lower pressure value towards the end of the expiration phase, so that a greater pressure difference is additionally obtained besides the steeper pressure gradient. With a selected time delay corresponding to half of the expiration time of 5 sec, namely, a time delay of 2.5 sec, a first upper pressure value of 5.2 hPa to 5.3 hPa and a first lower pressure value of about 4.6 hPa to 4.7 hPa are obtained in such a variant, for example, according to the above example for a patient with a body weight of 70 kg.

It can be postulated as a criterion for setting the upper pressure value and the lower pressure value that the positive end-expiratory pressure does not differ, on average, over the expiration phase for the patient from the positive end-expiratory pressure in case of constant stabilization.

The present invention will be explained in more detail now on the basis of a number of figures and the corresponding description of the figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
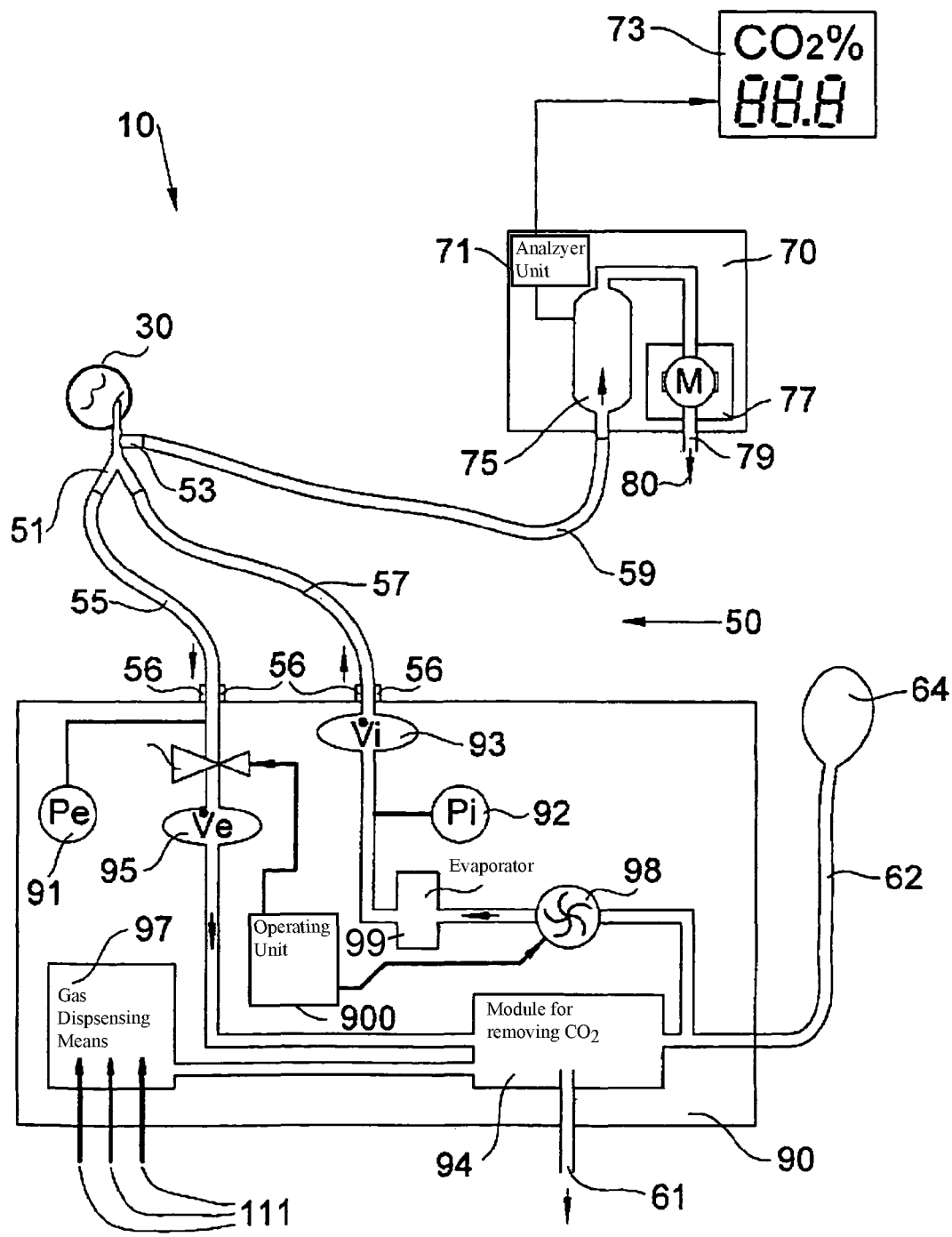
FIG. 1 is a schematic view of a respiratory system according to the invention

Referring to the drawings in particular, FIG. 1 schematically shows an arrangement 10 comprising a respiratory system 50 with a patient 30 and with an anesthesia apparatus 90 as well as with a measuring arrangement 70. Measuring arrangement 70 comprises in its interior a measuring unit 75, an analyzing and operating unit 71 as well as a corresponding display element 73. Furthermore, a pump 77, which suctions a quantity of air from the patient 30 via the Y-piece 51 and from the suction port 53 by means of a suction line 59 into the measuring arrangement 70 and passes same on to the ambient area 80 or into a discharge means provided for that purpose, is arranged in measuring arrangement 70. The respiratory system 50 is connected to the patient 30 via port elements 56 and a flexible tube system. The flexible tube system comprises a Y-piece 51 with a suction port 53, with an inspiratory tube section 57 and with an expiratory tube section 55. The measuring arrangement 70 is connected via the suction line 59 to the patient 30 by means of the Y-piece 51. Suction line 49 suctions off the air, namely, preferably the expired air, near the patient 30, and this air is then analyzed in measuring arrangement 70. Among other things, the carbon dioxide content is determined during this analysis and displayed on a display unit 73. An optical measuring means 75, which is designed, in conjunction with an operating and analyzing electronic unit 75, to determine the carbon dioxide gas concentration in the test gas collected, is present in the measuring arrangement 70. A plurality of elements are present in the respirator 90 to perform anesthesia and respiration of the patient 30 associated therewith. A gas dispensing means 97, into which gases, such as subsequently oxygen and nitrous oxide, as well as anesthetic gases can be fed from the outside via an access port 11, is provided. A manual breathing bag 64 with a feed line 62 is provided. The manual breathing bag 64 makes it possible for the anesthesiologist to perform manual respiration and anesthesia of the patient 30. An anesthetic evaporator 99, by means of which volatile anesthetics, for example, halothane, can be dispensed into the inspiratory air stream and fed to the patient 30 via the inspiratory tube section 57, is arranged in the gas path leading to the respiration drive 98.

A module 94 is provided, which performs the removal of carbon dioxide by means of a lime absorber, not shown in detail in FIG. 1, and which contains an anesthetic gas discharge line, not shown in detail in this FIG. 1, and a port 61 for discharging the anesthetic gas into the ambient area or to a gas collection means provided to this end in the hospital infrastructure.

Furthermore, the respiration drive 98 is designed in this embodiment as a radial compressor with the functionality of a pressure source. An anesthetic evaporator 99, by means of which volatile anesthetics, for example, halothane, are dispensed into the inspiratory air stream and to the patient 30 via the inspiratory tube section 57, is arranged in the gas path following the respiration drive 98. An inspiratory flow sensor 93, an expiratory flow sensor 95, a controlled expiratory valve 96 and a pressure sensor 91 arranged on the expiration side are provided as the sensor system and actuator system.

Furthermore, an operating and actuating unit 900 is provided, which actuates the actuator system 96 and the respiration drive 98 and detects and further processes the signals of the sensor system 91, 92, 93, 95. The data connections necessary for the detection of the sensor system 91, 92, 93, 95 are not shown in this schematic view according to FIG. 1.

FIGS. 2 through 5 show a time curve of breathing cycles of a patient. The respiration pressure, volume flow and carbon dioxide concentration $C_{CO_2}$) measured by suction by the measuring arrangement are shown in a time synchronicity.

Figure 2:
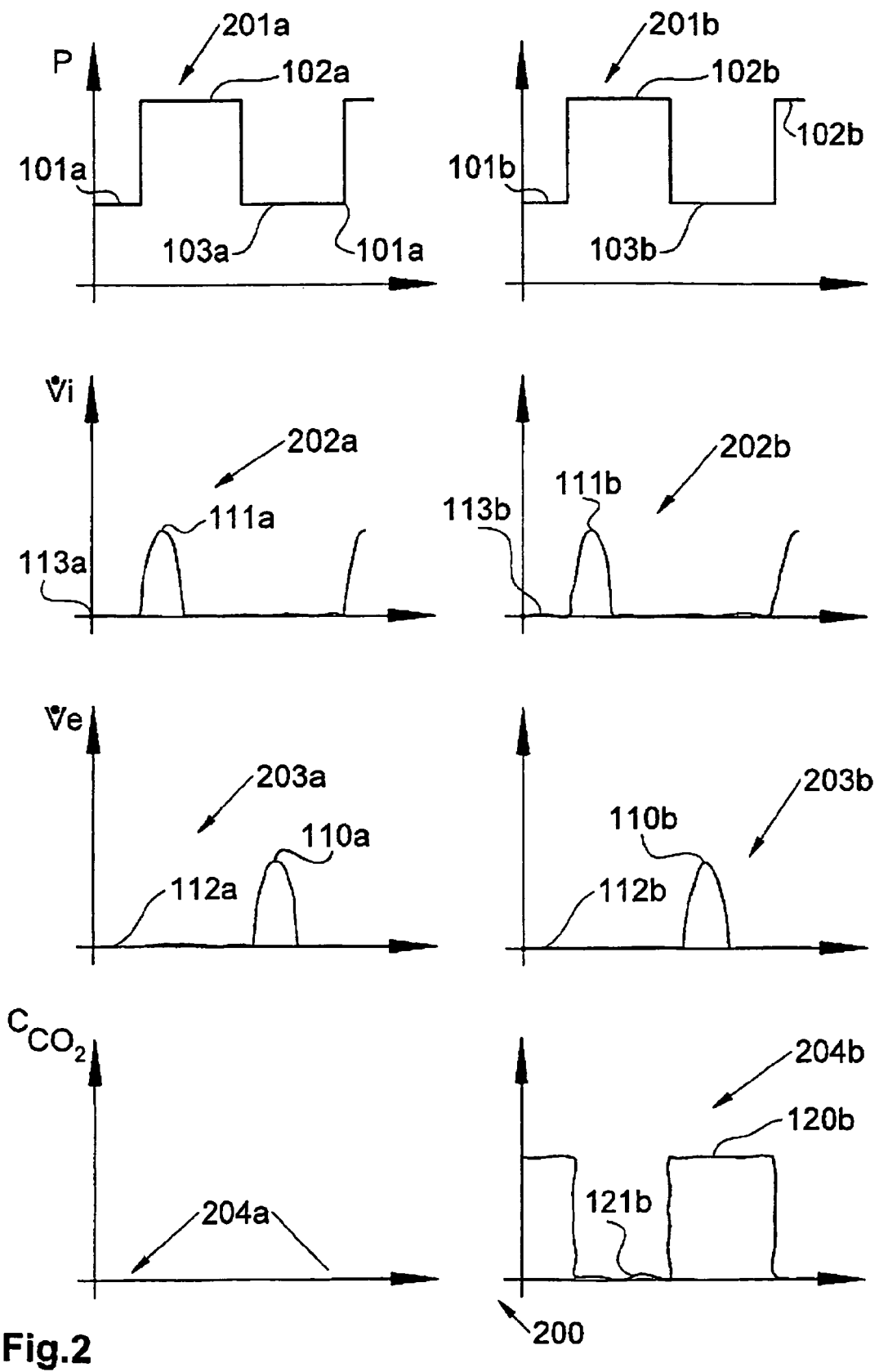
FIG. 2 is a first curve of the pressure, flow and carbon dioxide concentration ($C_{CO_2}$) over two breathing cycles of a patient without adjustment of the positive end-expiratory pressure.
Figure 3:
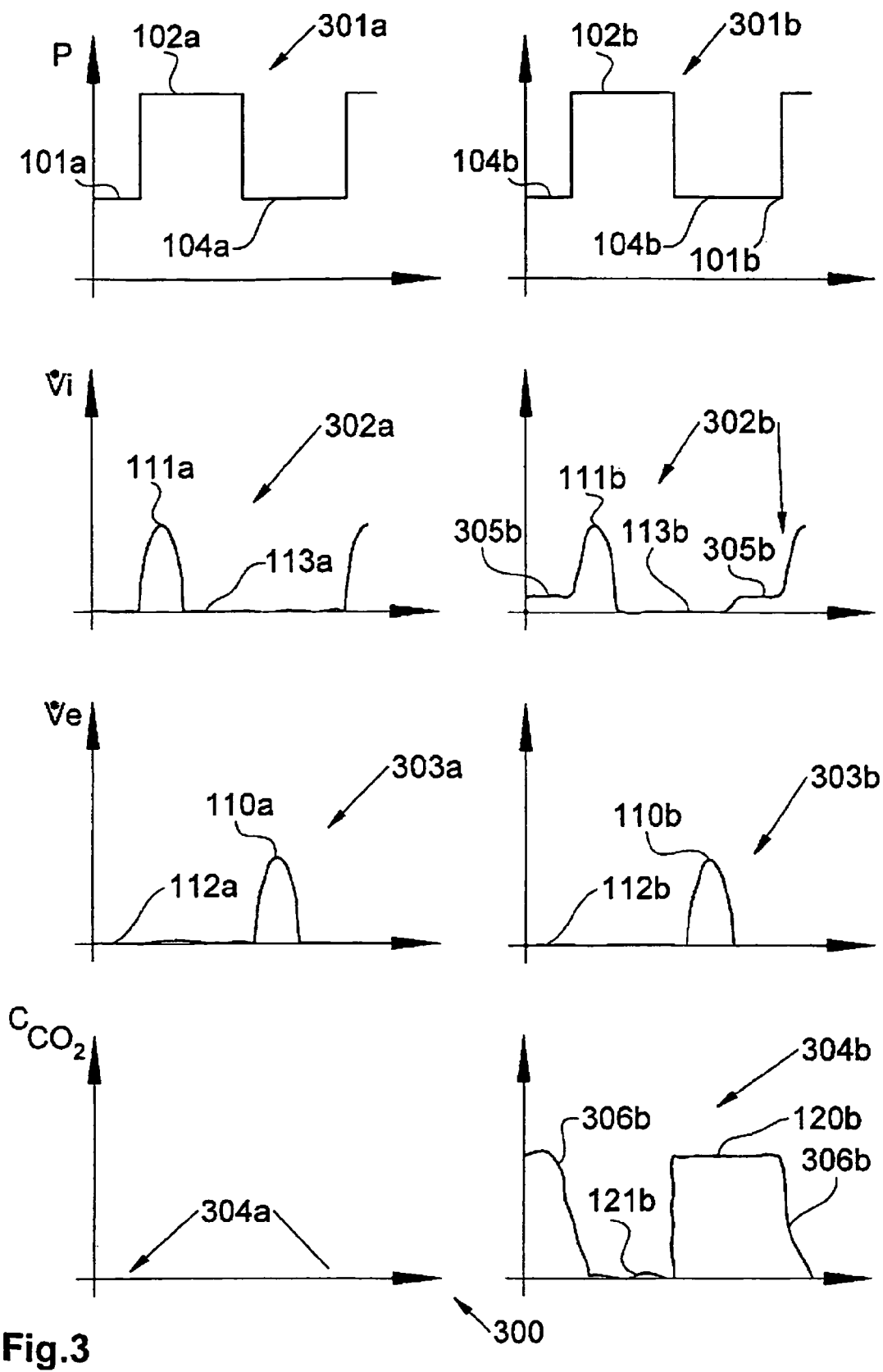
FIG. 3 is a second curve of the pressure, flow and carbon dioxide concentration ($C_{CO_2}$) over two breathing cycles of a patient with constant adjustment of the positive end-expiratory pressure.
Figure 4:
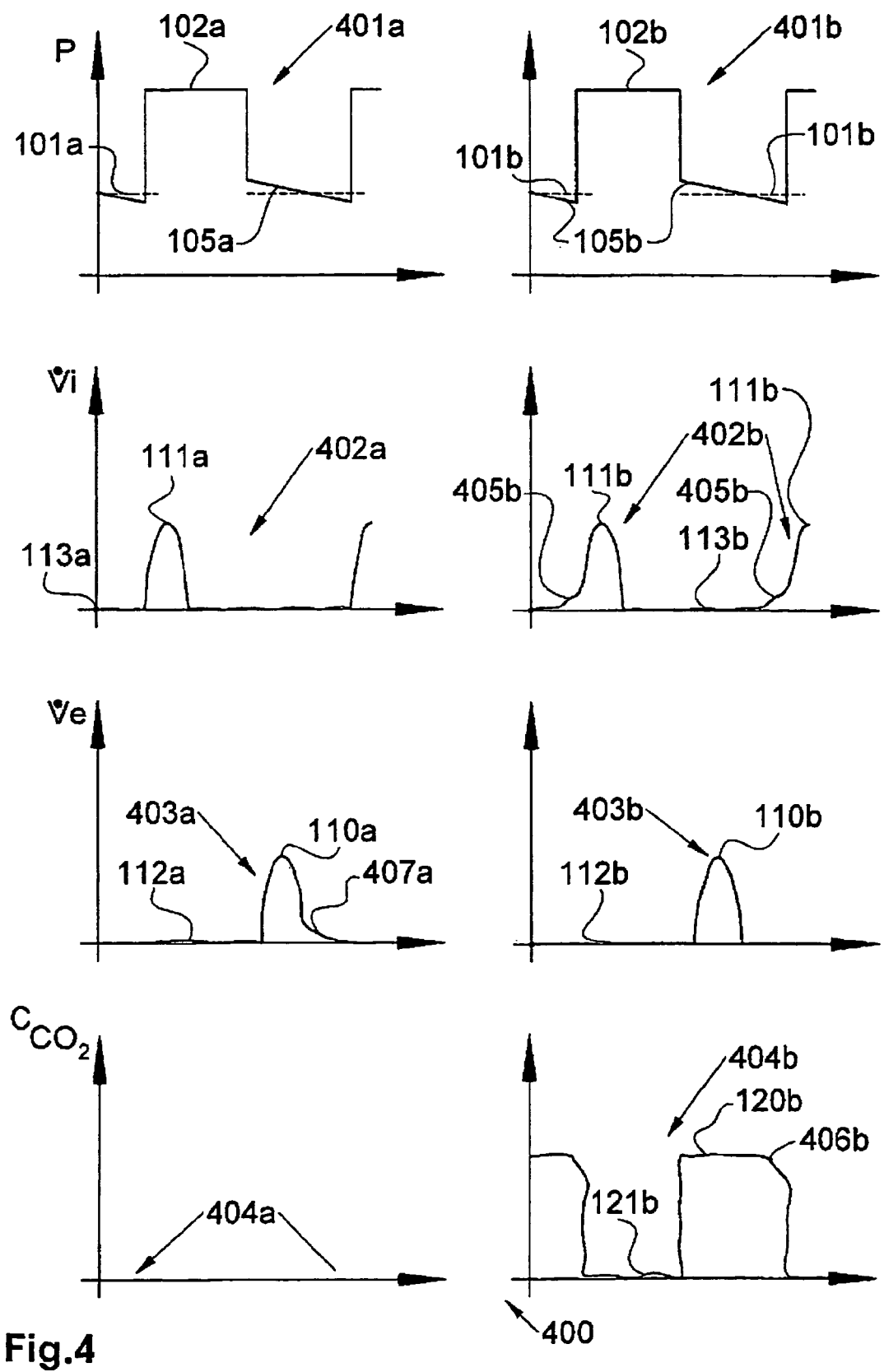
FIG. 4 is a third curve of the pressure, flow and carbon dioxide concentration ($C_{CO_2}$) over two breathing cycles of a patient with adjustment of the positive end-expiratory pressure according to a dropping pressure curve.
Figure 5:
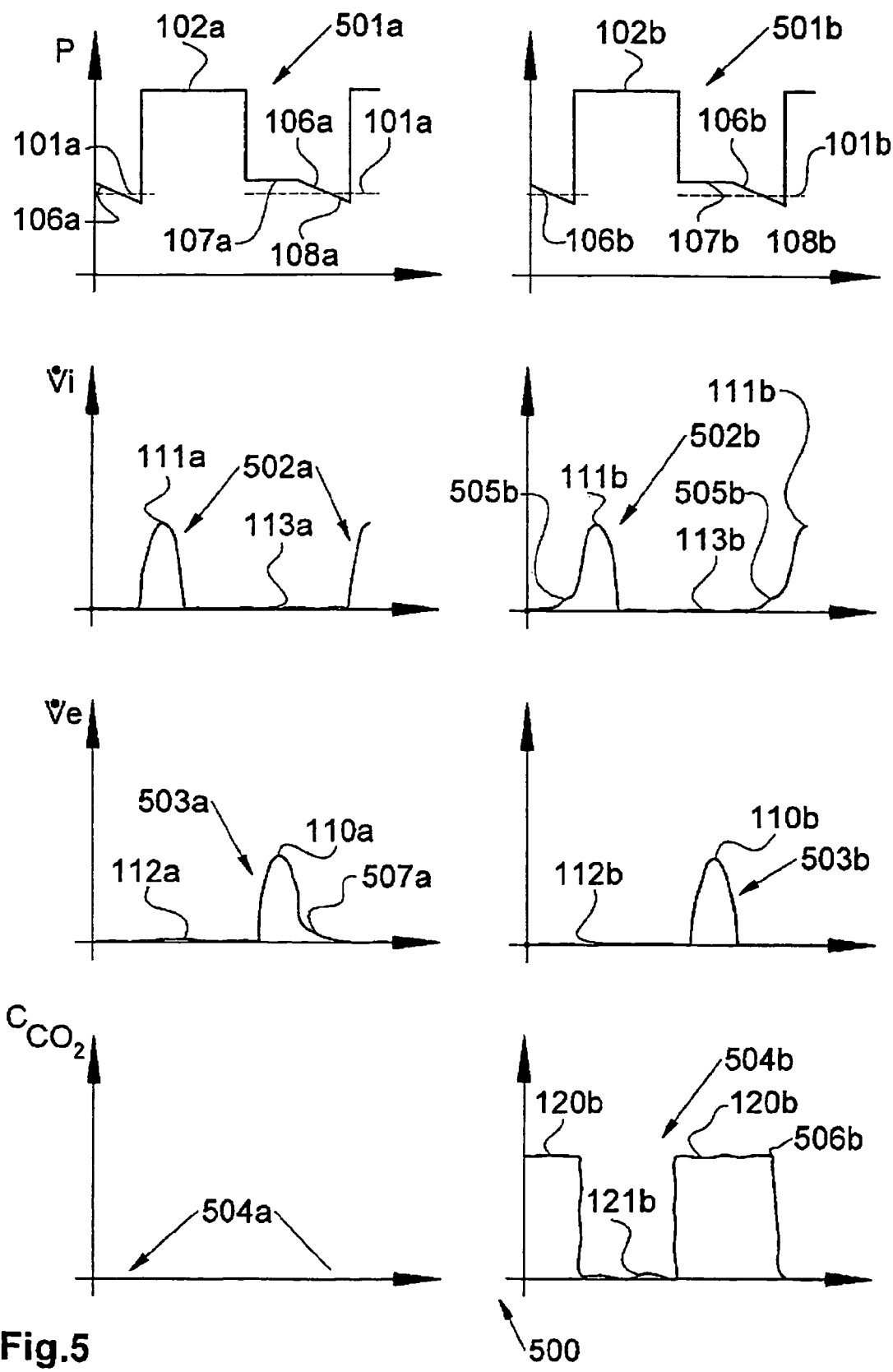
FIG. 5 is a variant of the curve according to FIG. 4.

FIG. 2 shows an embodiment in which no stabilization of the PEEP pressure takes place. FIG. 3 shows an embodiment in which regulating to the PEEP pressure takes place, wherein the PEEP level is maintained at a constant value during the expiration phase. FIG. 4 shows an embodiment in which the PEEP pressure is stabilized, wherein the stabilization is actuated according to a dropping desired pressure ramp. FIG. 5 shows a first variant according to FIG. 4, in which the PEEP pressure is stabilized, wherein the stabilization takes place at a constant level, and stabilization takes place according to a dropping desired pressure ramp in a second time period, subsequently to the first time period.

FIGS. 2 through 5 will be described in more detail now in a general, introductory description of the figures. Furthermore, the features in common and differences in FIGS. 2, 3, 4, 5 are explained. A time curve of the respiration pressure (P) of the inspiratory volume flow ($\dot{V}_I$), of the expiratory volume flow $\dot{V}_e$) and of the carbon dioxide concentration ($C_{CO_2}$) are shown in an arrangement 200, 300, 400, 500 of six diagrams. The three diagrams arranged one under another on the left side show the schematic curve of the respiration pressure (P), of the inspiratory volume flow ($\dot{V}_I$), of the expiratory volume flow $\dot{V}_e$) and of the carbon dioxide concentration ($C_{CO_2}$), measured by the measuring arrangement 70 (FIG. 1), with the volume flow suction through the suction line 59 (FIG. 1) by means of pump 77 (FIG. 1) into the measuring arrangement 70 (FIG. 1) not activated. The three diagrams arranged one under the other on the right show the schematic curve of the respiration pressure (P), of the volume flows ($\dot{V}_I$) and $\dot{V}_e$) as well as the curve of the carbon dioxide concentration ($C_{CO_2}$), measured in measuring arrangement 70 (FIG. 1) with the volume flow suction through the suction line 59 (FIG. 1) by means of pump 77 (FIG. 1) into the measuring arrangement 70 (FIG. 1) activated.

The diagrams (P, $\dot{V}_I$, $\dot{V}_e$, $C_{CO_2}$) arranged on the left side are marked by the use of reference numbers provided with suffix a. The diagrams arranged on the right side are marked by the use of reference numbers provided with suffix b. The reference numbers for the diagrams are selected in this common description of the figures such that assignment to the corresponding figure is indicated by the reference numbers of the diagrams. Elements identical in FIGS. 2 through 5 are provided with the same reference numbers in all FIGS. 2, 3, 4, 5.

Thus, the reference numbers of the diagrams (P, $\dot{V}_I$, $\dot{V}_e$, $C_{CO_2}$) begin with 200 for FIG. 2, with 300 for FIG. 3, with 400 for FIG. 4 and with 500 for FIG. 5. Expiratory pressure curves (P) 201a are without activated volume flow suction 59 (FIG. 1) and expiratory pressure curves 201b are with activated volume flow suction 59 (FIG. 1) by the measuring arrangement 70 (FIG. 1) in the diagram synopses 200, 300, 400, 500 in the figures.

Further, the diagram synopses 200, 300, 400, 500 show inspiratory volume flow curves ($\dot{V}_I$) 202a, 302a, 402a, 502a and expiratory volume flow curves $\dot{V}_e$) 203a, 303a, 403a, 503a without activated volume flow suction 59 (FIG. 1) as well as inspiratory volume flow curves ($\dot{V}_I$) 202b, 302b, 402b, 502b and expiratory volume flow curves $\dot{V}_e$) 203b, 303b, 403b, 503b with activated volume flow suction 59

(FIG. 1) corresponding in time with the pressure curves (P) 201a, 201b, 301a, 301b, 401a, 401b, 501a, 501b.

Corresponding to the pressure and volume flow curves, but with a time delay due to the volume flow suction, the carbon dioxide concentrations ($C_{CO_2}$) 204a, 304a, 404a, 504a are shown without activated volume flow suction and the carbon dioxide concentrations ($C_{CO_2}$) 204b, 304b, 404b, 504b with activated volume flow suction.

Without activated volume flow suction or without the measuring arrangement 70 (FIG. 1) being connected to the respiratory system 50 (FIG. 1) at the patient 30 (FIG. 1), no carbon dioxide measured signals are present. No curves of the carbon dioxide concentrations ($C_{CO_2}$) 204a, 304a, 404a, 504a are therefore visible in the diagrams that are shown on the left side in FIGS. 2 through 5, marked with suffix a. The diagrams 204a, 304a, 404a, 504a are correspondingly shown for the sake of clarity and completeness only.

The curves 201a, 201b, 202a, 202b, 203a, 203b, 204a, 204b of a technical embodiment of an anesthesia apparatus 90 (FIG. 1) are shown in FIG. 2 with a measuring arrangement 70 (FIG. 1) in the diagram synopsis 200, in which the pressure, especially the residual pressure during the expiration phase, is not stabilized. Expiratory pressure levels 101a, 101b are shown in the pressure curves 201a, 201b as an unregulated curve of a 3a, of a 3b in the form of a desired value or of a set value. The carbon dioxide concentration ($C_{CO_2}$) curves 204 shown as well as the curves of the inspiratory and expiratory volume flows ($\dot{V}_{I,e}$) 202a, 202b, 203a, 203b, which are shown in this diagram synopsis 200, are actual values based on measurements. The corresponding curves of the volume flows ($\dot{V}_{I,e}$) 202a, 202b, 203a, 203b have no influence due to the volume flow suction in this diagram synopsis 200. The maximum levels 111a, 111b and the basic levels 113a, 113b of the inspiratory volume flow ($\dot{V}_I$) 202a, 202b as well as the maximum levels 110a, 110b and the basic levels 112a, 112b of the expiratory volume flow ($\dot{V}_e$) 203a, 203b correspond to the respective corresponding curve of the inspiratory and expiratory pressure levels 102a, 102b, 103a, 103b in the pressure curves 201a, 202b.

The carbon dioxide concentration ($C_{CO_2}$) likewise corresponds to the pressure curve 202b with the basic level 121b and the maximum level 120b, without the maximum having appreciable discontinuities or signal rounding over the time course of expiration.

FIG. 3 shows the curves 301a, 301b, 302a, 302b, 303a, 303b, 304a, 304b of a technical embodiment of an anesthesia apparatus 90 (FIG. 1) and of a measuring arrangement 70 (FIG. 1) in the diagram synopsis 300, in which the pressure is stabilized during the inspiration time and during the expiration time, and especially the positive end-expiratory pressure (PEEP) is stabilized during the expiration phases after a constant curve 104a, 104b. Leaks, such as those occurring due to the activated volume flow suction 59 (Figure) of the measuring arrangement 70 (FIG. 1), as well as leaks in the respiratory system 50 (FIG. 1) and in the gas feed 51, 53, 54, 55, 56, 57 (FIG. 1) to the patient 30 (FIG. 1) are compensated by this regulation. The representations of the pressure curves 301a, 301b, just as the curves of the volume flows ($\dot{V}_{I,e}$) 302a, 302b, 303a, 303b and the curves of the carbon dioxide concentrations ($C_{CO_2}$) 304b represent time curves based on measured values determined by means of the sensor system in this diagram synopsis 300. The inspiratory and expiratory volume flow curves ($\dot{V}_{I,e}$) 303a, 302a with the basic level 112a, 113a and the maximum level 111a, 110a without activation of the volume flow suction to the measuring arrangement 70 (FIG. 1) show no essential differences from the curves 203 according to FIG. 2. The expiratory volume flow ($\dot{V}_e$) 303b with the maximum level 112b and the basic level 110b shows, with volume flow suction activated, no differences from the expiratory volume flow curve ($\dot{V}_e$) 303a, 112a, 110a without the volume flow suction being activated. The inspiratory volume flow ($\dot{V}_I$) shows, besides the maximum level 111b and the basic level 113b, a deviation 305b at the end of the expiration phase. A quantity of gas is removed from the respiratory system 50 (FIG. 1) by the volume flow suction. Inspiratory gas, which is detected during its flow through the inspiratory flow sensor 91 (FIG. 1) and its curve 302 thus becomes visible as a deviation 305b in the form of an additional rate of flow 305b at the end of expiration, is fed again due to the adjustment of the PEEP by the respiration drive 98 (FIG. 1), actuated by the operating and analyzing unit 900 (FIG. 1). This additional flow rate 305b causes the quantity of gas expired by the patient 30 (FIG. 1) at the Y-piece 51 (FIG. 1) to be mixed with fresh inspiration gas. This mixing causes a reduction of the carbon dioxide concentration ($C_{CO_2}$) at the Y-piece 51 (FIG. 1), because the carbon dioxide is removed from the gas expired by the patient 30 (FIG. 1) due to the removal of carbon dioxide in module 94 (FIG. 1) of the anesthesia apparatus 90 (FIG. 1) and gas free from carbon dioxide is thus delivered to the patient 30 (FIG. 1) for inspiration. This reduction of the carbon dioxide concentration ($C_{CO_2}$) becomes visible in the carbon dioxide concentration ($C_{CO_2}$) curve 304b as a drop in the concentration curve 306b at the end of expiration from the maximum level 120b of the expiratory carbon dioxide concentration ($C_{CO_2}$).

FIGS. 4 and 5 show the curves 401a, 401b, 402a, 402b, 403a, 403b, 404a, 404b, 501a, 501b, 502a, 502b, 503a, 503b, 504a, 504b of a technical embodiment of an anesthesia apparatus 90 (FIG. 1) and of a measuring arrangement 70 (FIG. 1) in the diagram synopses 400, 500, in which the positive end-expiratory pressure (PEEP) is not regulated at a constant value, unlike in the technical embodiment according to FIG. 3, but it is regulated in such a manner that the regulated pressure value is stabilized to a higher value at the beginning of expiration than the regulated pressure value at the end of expiration. The difference in the pressure levels between the beginning and the end of the expiration phase is achieved in the technical embodiments according to FIGS. 4 and 5 by the PEEP pressure being reduced over time during the expiration phase. This reduction of the PEEP may take place, as can be seen in the diagram synopsis 400, right at the beginning according to a dropping ramp 105a, 105b. However, the reduction may also be implemented according to a curve 106a, 106b according to FIG. 5 and the diagram synopsis 500 with a constant component 107a, 107b at the beginning of the expiration phase and with a dropping component 108a, 108b beginning during the duration of the expiration phase.

The shape of the pressure curves 105a, 106a, 105b, 106b during the expiration phase according to FIGS. 4 and 5 is determined in the embodiment of the level at the beginning as well as at the end of the expiration as well as in the embodiment of the dropping component as well as of the constant component of the curve on the basis of the expiratory pressure level 101a, 101b. The expiratory pressure level 101a, 101b indicated by broken lines in FIGS. 4 and 5 corresponds, on average, to the curves 105a, 105b, 106a, 106b, so that there will be no difference for the patient 30 (FIG. 1) compared to a constant PEEP stabilization 104a, 104b according to FIG. 3 in the pressure balance of the (PEEP) pressure at the patient during each expiration phase. Due to the fact that the pressure level is reduced during expiration, the patient 30 (FIG. 1) is enabled to continue to breathe out towards the end of the expiration until nearly the beginning of the next inspiration, because the pressure level in the lungs 26 (FIG. 1) of the patient 30 (FIG. 1) is likewise lowered according to the curve of the dropping ramp 105a, 105b, 106a, 106b, 108a, 108b. This additional and also longer-lasting expiration reaches the Y-piece 51 (FIG. 1) and, via the suction line 59 (FIG. 1), the measuring arrangement 70 (FIG. 1). Mixing of expired gas with fresh inspiration gas, adjusted on the basis of the volume flow suction, is thus avoided at the Y-piece 51 (FIG. 1), so that, unlike in the case of a constant stabilization 104a, 104b of the PEEP according to FIG. 3, the reduction of the carbon dioxide concentration ($C_{CO_2}$) in the concentration curve 404b, 504b will be recognized in a less significant manner as a drop 406b or only insignificantly as a drop 506b in case of activated volume flow suction. Thus, as it were, a constant display situation arises for the user concerning the carbon dioxide concentration ($C_{CO_2}$) being displayed over the entire duration of expiration.

There is a steeper gradient of the dropping component 108a, 108b of the pressure curve in the curve 106a, 106b in FIG. 5 compared to the curve 105a, 105b in FIG. 4 due to the presence of the constant component 107a, 107b of the pressure curve at the beginning. This steeper gradient 108a, 108b still enables expiration by the patient also at the end of the expiration phase, so that the reduction at the Y-piece 51 (FIG. 1) with adjusted fresh inspiration gas can take place even less. This is visible from the differences between the dropping curves 406b, 506b between the technical embodiments according to FIG. 4 and FIG. 5. The diagrams of the volume flows ($\dot{V}^V_{L_e}$) 402b, 403b, 502b, 503b on the right sides in FIGS. 4 and 5 show only slight differences from the curves 202b, 203b compared to the technical embodiment with unregulated PEEP according to FIG. 2. This arises from the fact that the adjustment of the PEEP causes, just as in FIG. 3, at the end of the expiration an inspiratory volume flow ($\dot{V}_I$), which is represented in the form of a deviation or of a forerun 405b, 505b as an additional flow rate besides the maximum levels 111b and the basic levels 113b of the inspiratory volume flow. With the volume flow suction not activated, the dropping curve 401a, 501b in the diagrams on the left sides of FIGS. 4 and 5 causes the quantity of gas still being expired by the patient 30 (FIG. 1) at the end of expiration not to be suctioned off at the Y-piece 51 (FIG. 1) of the arrangement 70 (FIG. 1) but to reach via the expiratory tube section 55 (FIG. 1) the anesthesia apparatus 90 (FIG. 1) and to be detected by the expiratory flow sensor 95 (FIG. 1) there. This can be seen as a overrun of the expiratory volume flow 407a, 507a in the curve of the expiratory flow rate 402a, 502a in the diagram synopses 400, 500 for the left sides of FIGS. 4 and 5.

FIGS. 6a, 6b, 6c and 6d show technical embodiment variants according to FIGS. 4 and 5 as well as further technical embodiment variants, in which the regulated positive end-expiratory pressure (PEEP) is reduced at the end of the expiration phase compared to the beginning.

Figure 6A:
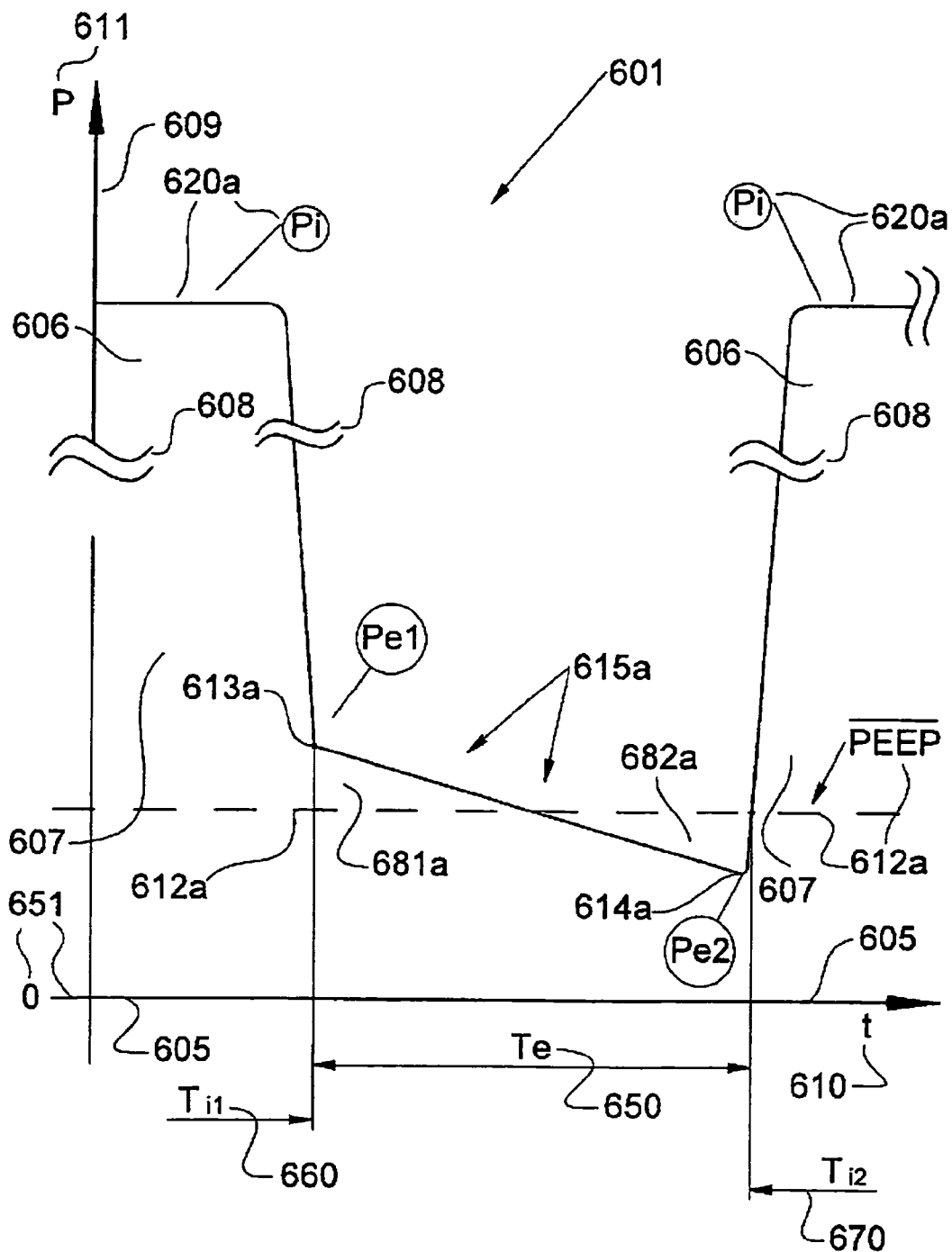
FIG. 6a is a detail views according to FIG. 5.
Figure 6B:
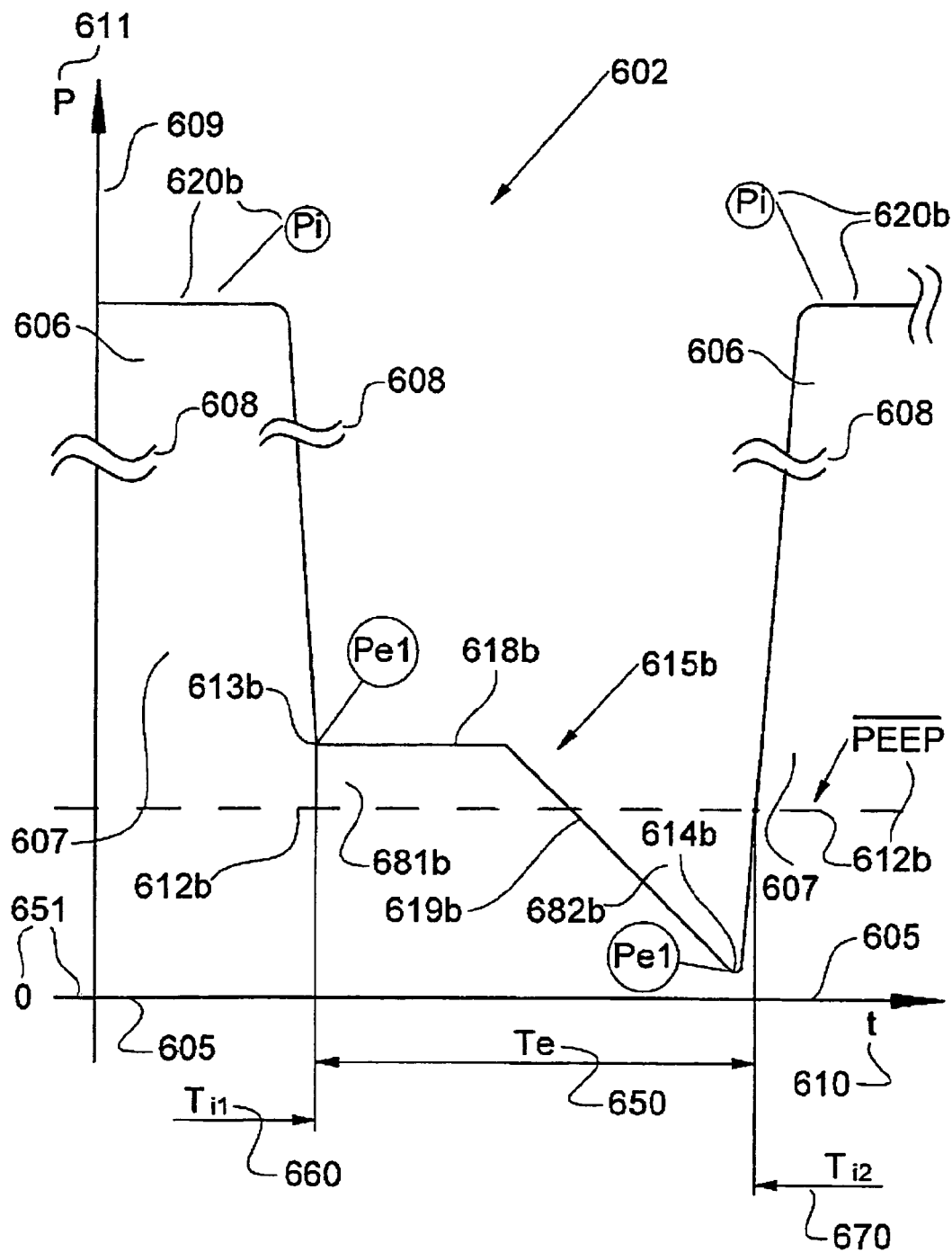
FIG. 6b is a detail views according to FIG. 4.
Figure 6C:
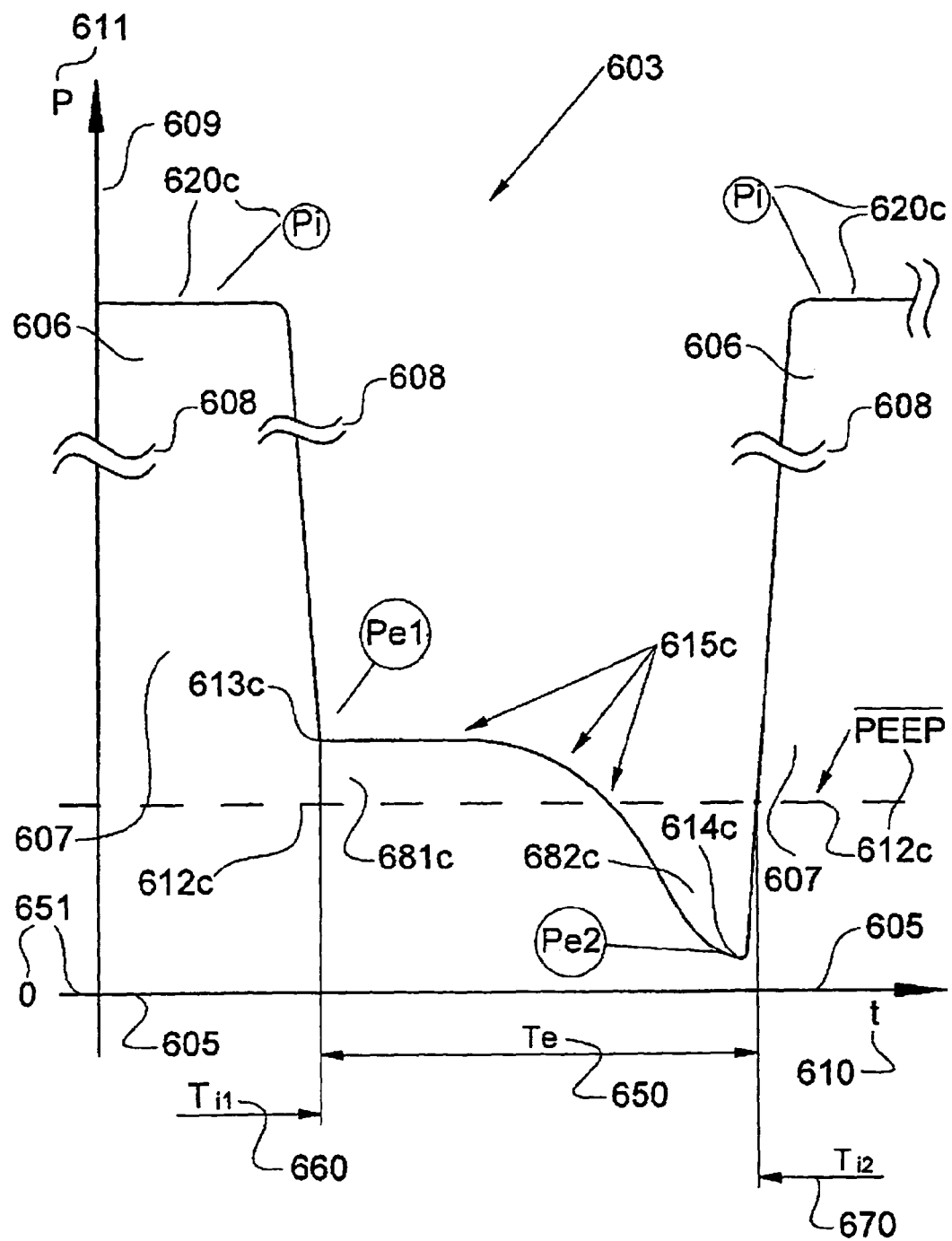
FIG. 6c is a detail views according to a modification of FIG. 5.
Figure 6D:
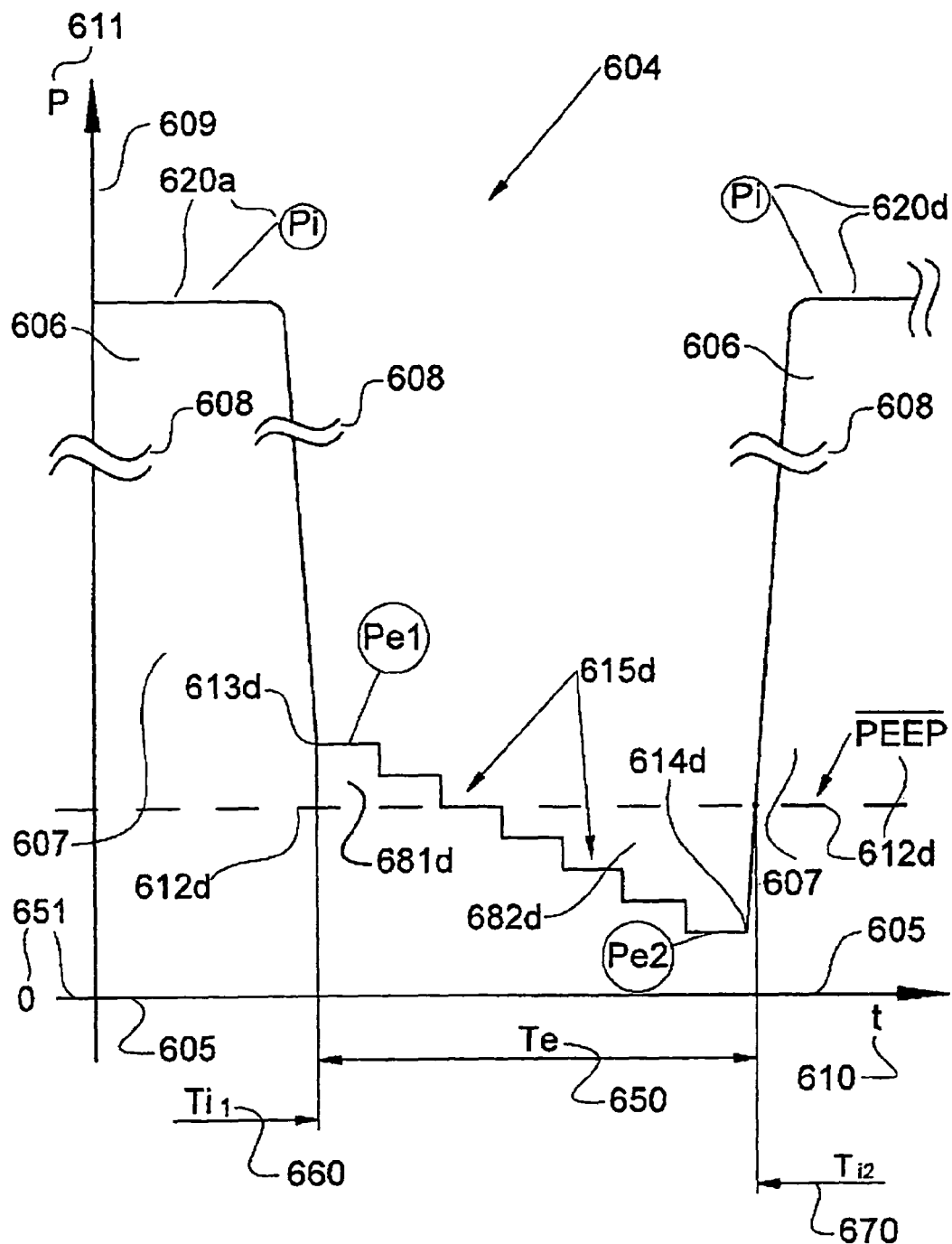
FIG. 6d is a detail views according to a modification of FIG. 4.

FIGS. 6a, 6b, 6c, 6d show variants of the regulation of the positive end-expiratory pressure (PEEP) according to the pressure curves shown in FIGS. 4 and 5. Identical elements in FIGS. 6a, 6b, 6c, 6d are designated by the same reference numbers of the same elements shown in FIGS. 2, 3, 4, 5. FIG. 6a shows a schematic pressure curve 601 at the patient according to the pressure curve 401b in FIG. 4. FIG. 6b shows a schematic pressure curve 602 at the patient according to the pressure curve 501b in FIG. 5. FIG. 6c shows a pressure curve 603 at the patient in a modified form according to the pressure curve 501b in FIG. 5. FIG. 6d shows a pressure curve 604 at the patient in a modified form according to the pressure curve 401b in FIG. 4.

The pressure curves 601, 602, 603, 604 in FIGS. 6a, 6b, 6c, 6d may be further adapted. In particular, combinations of the modified forms 603, 604 with one another and/or with the pressure curves 601, 602 are also covered in the sense of the present invention.

FIGS. 6a, 6b, 6c, 6d will be explained now in more detail in a common description of the figures in terms of the features they have in common and with illustration of the differences from each other in the technical embodiments of the regulation of the positive end-expiratory pressure (PEEP).

Identical reference numbers are used for identical elements in FIGS. 6a, 6b, 6c, 6d. The suffixes a, b, c, d used additionally at/in the reference numbers are used to make it possible to distinguish basically identical reference numbers and features in FIGS. 6a, 6b, 6c, 6d. The use of suffix a pertains to elements of FIG. 6a. The use of suffix b pertains to elements of FIG. 6b. The use of suffix c pertains to elements of FIG. 6c. The use of suffix d pertains to elements of FIG. 6d. Pressure curves beginning at the end of an inspiration with a first component 1 $T_{i1}$ 660 with an inspiratory pressure level $P_i$ 620, with an expiration time $T_e$ 650 following same and with a component 2 $T_{i2}$ 670 of the inspiration following next with the inspiratory pressure level $P_i$ 620 are plotted on the abscissa (x) 605 over time 610 in the pressure curves 601, 602, 603, 604 shown in FIGS. 6a, 6b, 6c, 6d.

Expiratory, dropping pressure curves 615a (FIG. 6a), 615b (FIG. 6b), 615c (FIGS. 6c) and 615d (FIG. 6d) are shown in the expiration time $T_e$ 650 shown. The schematic pressure curves 601, 602, 603, 604 are scaled as pressure 611 on an ordinate (y) 609. Ordinate 609 is divided by a separation sign 608 into two sections. The first section of ordinate 606 scales the inspiratory pressure level 620 in the expiration times $T_{i1}$ 660 and $T_{i2}$ 670. The second section of ordinate 607 is adapted in a different scaling of the positive end-expiratory pressure (PEEP) during the expiration time $T_e$ 650 in order to make it possible to represent the expiratory, dropping pressure curves in a graphic form in a suitable manner. The values of the inspiratory pressure levels 620 are selected to the identical in FIGS. 6a, 6b, 6c, 6d. The scaling of ordinate 609 and of the sections of the ordinates 606, 607 are selected to be identical and represented as being identical in FIGS. 6a, 6b, 6c, 6d. A zero level 651 is shown in FIGS. 6a, 6b, 6c, 6d as a reference for scaling the ordinate 609. Furthermore, a mean value of the positive end-expiratory pressure $\overline{PEEP}$ 612a, 612b, 612c, 612d is shown with reference to the zero level 651 in the form of a broken line. The starting values $P_{e1}$ 613a, 613b, 613c, 613d and the final values $P_{e2}$ 614a, 614b, 614c, 614d of the expiratory pressure at the beginning and at the end of the expiration time $T_e$ 650 are derived and determined from this mean value $(\overline{PEEP})$ 612 of the positive end-expiratory pressure. This determination of $P_{e1}$ 613a, 613b, 613c, 613d and of $P_{e2}$ 614a, 614b, 614c, 614d is performed in the technical embodiments according to FIGS. 6a, 6b, 6c, 6d on the basis of the predetermined mean value $\overline{PEEP}$ 612, the expiration time $T_e$ 650 as well as of the respective curve describing the pressure stabilization in FIGS. 6a, 6b, 6c, 6d, respectively. The mean value $\overline{PEEP}$ 612 of the end-expiratory pressure as well as the expiration time $T_e$ 650 and the inspiratory pressure level $P_i$ 620 will be obtained as different values for different types of patients, as it is explained in the description in Table 1 and in Table 2.

The pressure curve of the PEEP is shown in FIG. 6a over the expiration time $T_e$ 650 as a linear, dropping ramp 615a, which is dropping over the entire expiration time $T_e$ 650.

In FIG. 6b, the pressure curve of PEEP over the expiration time $T_e$ 650 is a two-part function curve 615b beginning with a time period of the curve with constant pressure level 618b and with a subsequent time period of the curve with dropping pressure 619b.

In FIG. 6c, the pressure curve of PEEP over the expiration time $T_e$ 650 as a modified form of the two-part function curve 615b according to FIG. 6b, and a constant time period and a dropping time period pass continuously over into each other after a progressively dropping function curve 615c. Such a progressively dropping function curve 615c can be formed in a suitable manner preferably by means of potential functions, exponential or logarithmic functions, as well as broken rational functions or in a special manner by means of combinations of potential functions, exponential, logarithmic or broken rational functions. A progressive drop of PEEP towards the end of the expiration phase causes the patient 30 (FIG. 1) to let expired, carbon dioxide-containing air flow to the Y-piece 53 (FIG. 1) over the entire expiration. Thus, there is no mixing with fresh inspiration gas at the Y-piece 53 (FIG. 1), so that there will be no drop in the carbon dioxide concentration ($C_{CO_2}$), unlike in case of stabilization to an unchanging, constant PEEP, as is shown in FIG. 3. The progressive drop 615c rather leads to the effect that there is no essential drop in the carbon dioxide concentration ($C_{CO_2}$) at the end of expiration, and this drop is comparable to the drop as it is shown in FIG. 5 in the expiratory $CO_2$ concentration curve 504b (FIG. 5).

FIG. 6d shows a pressure curve according to FIG. 6a in a modified form. The dropping curve 615d of the expiratory pressure during the expiration time $T_e$ 650 is a discontinuous curve. This means that the drop of PEEP during expiration is embodied as a discontinuous curve 615d dropping steps due to the pressure regulation in the operating and analyzing unit 900 (FIG. 1) rather than as a continuous function curve. Such a stepped or also stepwise lowering of PEEP arises, for example, from the digitization and/or quantification in digital and/or binary computing units (microcontrollers, processors, digital signal processors) on the basis of the bit resolutions used in these systems.

The mean PEEP values ($\overline{PEEP}$) 612a, 612b, 612c, 612d are selected as a first preset value and the duration of the expiration phase $T_e$ 650 is selected as a second preset value in FIGS. 6a, 6b, 6c, 6d. The starting value ($P_{e1}$) of the expiratory pressure 613a, 613b, 613c, 613d and the final value of the expiratory pressure ($P_{e2}$) 614a, 614b, 614c, 614d are set in conjunction with the respective selected shape of the pressure drop curve 615a, 615b, 615c, 615d. This setting is performed in FIGS. 6a, 6b, 6c, 6d such that the starting values ($P_{e1}$) 613a, 613b, 613c, 613d and the final values ($P_{e2}$) 614a, 614b, 614c, 614d are selected in conjunction with the curve 615a, 615b, 615c, 615d such that a first area 681a, 681b, 681c, 681d, defined between the mean PEEP ($\overline{PEEP}$) 612a, 612b, 612c, 612d and the curve 615a, 615b, 615c, 615d above the mean PEEP ($\overline{PEEP}$) 612a, 612b, 612c, 612d and a second area 682a, 682b, 682c, 682d, defined between the mean PEEP ($\overline{PEEP}$) 612a, 612b, 612c, 612d and the curve 615a, 615b, 615c, 615d below the mean PEEP ($\overline{PEEP}$) 612a, 612b, 612c, 612d agree in terms of superficial contents. Embodying a dropping pressure ramp according to FIGS. 6a, 6b, 6c, 6d, a positive end-expiratory pressure (PEEP) is obtained for the patient 30 (FIG. 1) due to this setting, and this positive end-expiratory pressure corresponds, on average, to the same positive end-expiratory pressure (PEEP) as in case of constant stabilization of the PEEP over the expiration phase, as is shown in FIG. 2, with the advantage that the measured carbon dioxide concentration ($C_{CO_2}$) does not drop towards the end of the expiration phase or it does not do so substantially.

While specific embodiments of the invention have been shown and described in detail to illustrate the application of the principles of the invention, it will be understood that the invention may be embodied otherwise without departing from such principles.

The invention claimed is:

1. A method for controlling the end-expiratory pressure at a patient in a respiratory system of an anesthesia apparatus or ventilator, the method comprising the steps of:
artificially, mechanically ventilating the patient by regulating pressure to the patient during an inspiration phase and during an expiration phase and wherein the pressure is regulated during the expiration phase such that the pressure is described by an at least partially dropping curve that drops from an upper pressure value following the inspiration phase to a lower pressure value from the end of the inspiration phase until the beginning of the next, following inspiration phase, wherein pressure is regulated during the expiration phase such that a positive end-expiratory pressure corresponds, on average, to a mean positive end-expiratory pressure provided by a constant stabilization of the positive end-expiratory pressure over the expiration phase, wherein a first area defined between the mean positive end-expiratory pressure and a portion of the dropping curve above the mean positive end-expiratory pressure is equal to a second area defined between the mean positive end-expiratory pressure and another portion of the dropping curve below the mean positive end-expiratory pressure.

2. A method in accordance with claim 1, wherein the dropping pressure from the upper pressure value to the lower pressure value is described by a linearly dropping curve and/or by a non-linear curve.

3. A method in accordance with claim 1, wherein the dropping pressure from a upper pressure value to a lower pressure value is described by a continuous curve and/or a discontinuous curve.

4. A method in accordance with claim 1, wherein the dropping pressure from the upper pressure value to the lower pressure value starts after a time delay with a constant pressure level.

5. A method in accordance with claim 1, wherein settings of the ventilator or anesthesia apparatus are used to determine the upper pressure value and to determine the lower pressure value, wherein a downward slope of said dropping curve is greater at an end of the expiration phase than said downward slope of said dropping curve at a beginning of the expiration phase.

6. A method in accordance with claim 5, wherein the settings of the anesthesia apparatus or ventilator comprise settings for at least one of the positive end-expiratory pressure and the ventilation rate and the inspiration to expiration ratio.

7. A method in accordance with claim 1, further comprising:
providing a patient connection including an inspiratory connection and an expiratory connection;

providing a gas pressure regulating arrangement comprising a controllable expiratory valve and a ventilation drive;
providing an expiratory pressure sensor;
providing an inspiratory pressure sensor;
providing an inspiratory flow sensor; and
controlling the controllable expiratory valve and the ventilation drive during operation such that the pressure curve is described during the expiration phase from the end of the inspiration phase from the upper pressure value to the lower pressure value by the at least partially dropping curve.

8. An anesthesia apparatus or ventilator comprising:
a patient connection;
a gas pressure regulating arrangement for regulating gas pressure at the patient connection; and
an operating and actuating unit connected to the gas pressure regulating arrangement and adapted to artificially mechanically ventilate the patient by regulating pressure to the patient during an inspiration phase and an expiration phase such that the expiration phase, from the end of the inspiration phase to the beginning of the following inspiration phase, is described by an at least partially dropping curve from an upper pressure value following the inspiration phase to a lower pressure value from the end of the inspiration phase until the beginning of the next, following inspiration phase, wherein the operating and actuating unit regulates the pressure during the expiration phase such that a positive end-expiratory pressure corresponds, on average, to a mean positive end-expiratory pressure provided by a constant stabilization of the positive end-expiratory pressure over the expiration phase, wherein a first area defined between the mean positive end-expiratory pressure and a portion of the dropping curve above the mean positive end-expiratory pressure is equal to a second area defined between the mean positive end-expiratory pressure and another portion of the dropping curve below the mean positive end-expiratory pressure.

9. An anesthesia apparatus or ventilator in accordance with claim 8, wherein the patient connection includes an inspiratory connection and an expiratory connection and the gas pressure regulating arrangement includes a controllable expiratory valve and a ventilation drive and further comprising:
an expiratory pressure sensor;
an inspiratory pressure sensor;
an inspiratory flow sensor, wherein the operating and actuating unit regulates the controllable expiratory valve and the ventilation drive during operation such that the pressure curve is described during the expiration phase from the end of the inspiration phase from the upper pressure value to the lower pressure value by the at least partially dropping curve.

10. An anesthesia apparatus or ventilator in accordance with claim 9, wherein the operating and actuating unit regulates the operation of the controllable expiratory valve and regulates the operation of the ventilation drive such that the at least partially dropping curve is one of a linear dropping curve and a nonlinear curve.

11. An anesthesia apparatus or ventilator in accordance with claim 9, wherein the operating and actuating unit regulates the operation of the controllable expiratory valve and regulates the operation of the ventilation drive such that the at least partially dropping curve is a continuous curve or a discontinuous curve.

12. An anesthesia apparatus or ventilator in accordance with claim 9, wherein the operating and actuating unit regulates the operation of the controllable expiratory valve and the ventilation drive such that the at least partially dropping curve starts with a constant pressure level and drops after a time delay.

13. An anesthesia apparatus or ventilator in accordance with claim 9, wherein the operating and actuating unit determines the upper pressure value and the lower pressure value as a function of settings of the ventilator or anesthesia apparatus.

14. An anesthesia apparatus or ventilator in accordance with claim 13, wherein the operating and actuating unit sets at least one of the positive end-expiratory pressure, the ventilation rate and the inspiration to expiration ratio as a setting and determines the upper pressure value and the lower pressure value based on the setting.

15. An anesthesia apparatus or ventilator in accordance with claim 8, wherein the pressure is regulated during the expiration phase such that during the expiration phase the pressure drops from said upper pressure value to a first intermediate pressure and the pressure drops from said first intermediate pressure value to a second intermediate pressure value and the pressure drops from said second intermediate pressure value to said lower pressure value, said second intermediate pressure value being greater than said lower pressure value and less than said first intermediate pressure value and less than said upper pressure value, said first intermediate value being less than said upper pressure value and greater than said second intermediate pressure value and greater than said lower pressure value.

16. An anesthesia apparatus or ventilator comprising:
a patient connection;
a gas pressure regulating arrangement for regulating gas pressure at the patient connection; and
an operating and actuating unit connected to the gas pressure regulating arrangement and configured to artificially mechanically ventilate the patient by regulating pressure to the patient during an inspiration phase and an expiration phase such that during said expiration phase, an end positive end-expiratory pressure at an end of the expiration phase is less than a beginning positive-end expiratory pressure at a start of the expiration phase, wherein said beginning positive-end pressure is decreased to at least one intermediate positive end-expiratory pressure via said operating and actuating unit during said expiration phase, said at least one intermediate positive end-expiratory pressure being less than said beginning positive-end pressure and greater than said end positive end-expiratory pressure, wherein a gradient of said at least partially dropping curve is greater at an end of the expiration phase than said gradient of said at least partially dropping curve at a beginning of the expiration phase, wherein said gradient of said dropping curve comprises more than constant subintervals.

17. An anesthesia apparatus or ventilator in accordance with claim 16, wherein said at least one intermediate positive end-expiratory pressure is decreased to at least another intermediate positive end-expiratory pressure via said operating and actuating unit during said expiration phase, said at least another intermediate positive end-expiratory pressure being greater than said end positive end-expiratory pressure and less than said at least one intermediate positive end-expiratory pressure and less than said beginning positive-end pressure.

* * * * *